United States Patent [19]

Philippossian et al.

[11] Patent Number: 4,469,698
[45] Date of Patent: Sep. 4, 1984

[54] DI- OR TRISUBSTITUTED XANTHINES WITH NEUROLEPTIC PROPERTIES AND COMPOSITION

[75] Inventors: Georges Philippossian, Lausanne; Marc Enslen, Yverdon, both of Switzerland

[73] Assignee: Societe d'Assistance Technique pour Produits Nestle S.A., Lausanne, Switzerland

[21] Appl. No.: 470,301

[22] Filed: Feb. 28, 1983

Related U.S. Application Data

[63] Continuation of Ser. No. 255,212, Apr. 17, 1981, abandoned.

[30] Foreign Application Priority Data

May 2, 1980 [CH] Switzerland .................. 3431/80

[51] Int. Cl.³ .................. C07D 473/04; A61K 31/52
[52] U.S. Cl. .................. 424/253; 544/267; 544/265
[58] Field of Search .................. 424/253; 544/267, 265

[56] References Cited

U.S. PATENT DOCUMENTS 4,089,959  5/1978  Diamond .................. 424/253

FOREIGN PATENT DOCUMENTS 766754  1/1955  United Kingdom .

1561005  2/1980  United Kingdom .

Primary Examiner—Nicholas S. Rizzo
Attorney, Agent, or Firm—Vogt & O'Donnell

[57] ABSTRACT

The invention relates to xanthines corresponding to the formula

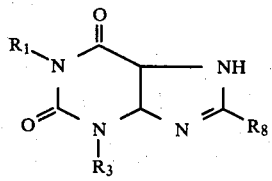

and physiologically acceptable salts thereof, in which $R_1$ represents $C_2$–$C_4$-alkyl, $C_3$–$C_4$-isoalkyl, $CH_2$-($C_2$–$C_3$-alkenyl) or $CH_2$-($C_3$-isoalkenyl);

$R_3$ represents $C_3$–$C_5$-alkyl, $C_3$–$C_5$-isoalkyl, $CH_2$-($C_2$–$C_4$-alkenyl) or $CH_2$-($C_3$–$C_4$-isoalkenyl);

$R_8$ represents H, methyl or ethyl;

with the proviso that
(1) when $R_8$ represents H, $R_1$ is allyl and
(2) $R_1$ and $R_3$ cannot both represent butyl or allyl at the same time.

The compounds show non-specific or anxiolytic sedative activity.

27 Claims, No Drawings

DI- OR TRISUBSTITUTED XANTHINES WITH NEUROLEPTIC PROPERTIES AND COMPOSITION

This is a continuation of application Ser. No. 255,212, filed Apr. 17, 1981, now abandoned.

This invention relates to new pharmacologically active di- and tri-substituted xanthines, to processes for their preparation and to a medicament containing them.

Xanthines are known for their stimulating effect on the central nervous system. Examples of xanthines are caffeine and theophylline.

Certain xanthines have been described for their spasmolytic activity, for example in German Patent Application No. 2,713,389 or in European Patent Application Publication No. 7735.

It has now been found that, unlike the therapeutically used psychostimulating xanthines, certain new 1,3- and 1,3,8-substituted xanthines show sedative or anxiolytic activity at a remarkable activity level and without any side effects being observed at the effective doses (ED50) for the neuroleptic activity.

Some of the new xanthines show additional diuretic, anti-allergic, bronchodilatory or anti-histamine activity in minimal effective doses, i.e. producing a significant response in base screening, distinctly greater than the effective doses (ED50) for the neuroleptic effect, in other words this additional activity does not in any way diminish the value of the neuroleptic activity.

The compounds according to the invention are xanthines corresponding to the general formula

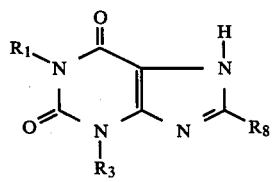
(I)

and physiologically acceptable salts thereof in which
$R_1$ represents $C_2$–$C_4$-alkyl, $C_3$–$C_4$-isoalkyl, $CH_2$-($C_2$–$C_3$-alkenyl) or $CH_2$-($C_3$-isoalkenyl);
$R_3$ represents $C_3$–$C_5$-alkyl, $C_3$–$C_5$-isoalkyl, $CH_2$-($C_2$–$C_4$-alkenyl) or $CH_2$-($C_3$–$C_4$-isoalkenyl);
$R_8$ represents H, methyl or ethyl;
with the proviso that
(1) when $R_8$ represents H, $R_1$ represents allyl and
(2) $R_1$ and $R_3$ cannot both represent butyl or allyl at the same time.

Preferred compounds corresponding to general formula (I) are those in which $R_1$ represents allyl, propyl or isobutyl, $R_3$ represents propyl, butyl or isobutyl and $R_8$ represents methyl, particularly preferred compounds being 1-allyl-3-butyl-8-methyl xanthine, 1-propyl-3-butyl-8-methyl xanthine, 1-allyl-3-isobutyl-8-methyl xanthine, 1,3-diisobutyl-8-methyl xanthine, 1,3-dipropyl-8-methyl xanthine, 1-propyl-3-isobutyl-8-methyl xanthine and 1-allyl-3-propyl-8-methyl xanthine and physiologically acceptable salts thereof.

Compounds of formula (I) in which $R_1$ represents allyl, $R_3$ represents butyl and $R_8$ represents H also constitute a preferred class.

In the context of the invention, physiologically acceptable salts of the compounds corresponding to general formula (I) are understood to be the salts which these compounds form with pharmaceutically acceptable bases. The salts in question are salts the cations of which are harmless to animal organisms and do not cause any side effects in therapeutic doses. Salts such as these include the salts of alkali metals, such as sodium, potassium, pharmaceutically acceptable salts of ammonium and amines known to the expert. These salts may be prepared by heating the compound of general formula (I) in the presence of the appropriate base and in the presence or absence of a solvent, preferably followed by recrystallisation.

The compounds according to the invention may be prepared by one of the following processes:
(a) A uracil corresponding to the formula

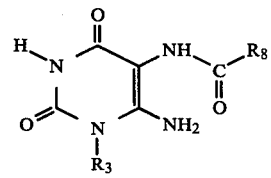
(II)

is reacted with an alkylating agent of the formula $R_1$—X where $R_1$, $R_3$ and $R_8$ have the same meaning as in general formula (I), except that neither $R_1$ nor $R_3$ may be isopropyl, and where X is a halogen atom, preferably bromine, or monosulphate or disulphate or p-toluene sulphonate and the compound obtained is cyclised. The reaction is preferably carried out in a solvent suitable for all the reactants, such as for example dimethyl formamide (DMF), dimethyl sulphoxide (DMSO) or hexamethyl phosphorotriamide (HMPT) at a temperature in the range from 20° to 40° C. and in the presence of an alkali metal hydroxide, for example sodium hydroxide in solid form. The reaction is preferably carried out in DMF at 20° C. in accordance with the following scheme:

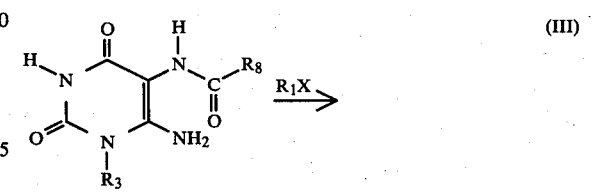
(III)

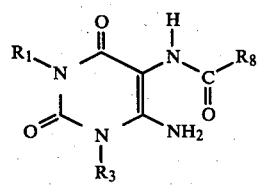

The product corresponding to general formula (III) is then cyclised in a boiling solution of alkali metal hydroxide in accordance with the following reaction scheme:

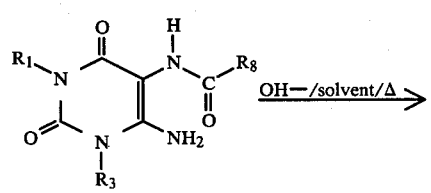
(I)

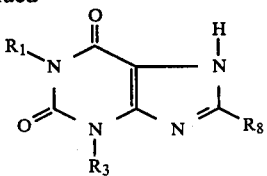

Although it is possible to isolate the intermediate of general formula (III), it is preferred to carry out cyclisation directly without isolating or purifying the intermediate in question. To this end, the reaction medium is neutralised and the solvent evaporated, after which the residue is dissolved in an alkali hydroxide solution and the resulting solution heated to reflux temperature.

The starting uracil of general formula (II) may be prepared by conventional methods, for example Traube's method (Chem. Ber. 33, 1371 and 3055, 1900) in which a urea $$R_3-NH-\overset{O}{\underset{\|}{C}}-NH_2$$

is reacted with cyanoacetic acid in acetic anhydride, the acetic anhydride is evaporated and the residue treated with sodium hydroxide, leading to a 1-alkyl-6-aminouracil which is then converted into the compound of general formula (II) in accordance with the following reaction scheme:

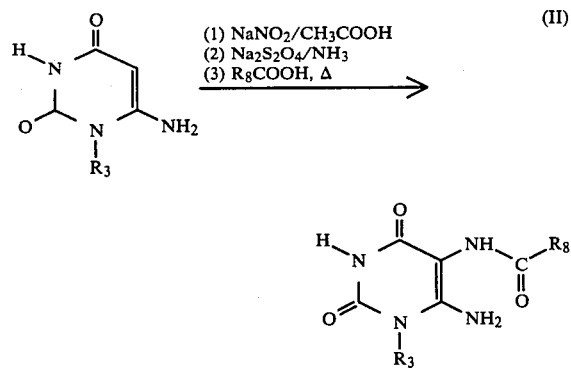

(b) In a variant of the above-described process, a compound corresponding to general formula (I), in which at least one of the substituents $R_1$ and $R_3$ is alkenyl or isoalkenyl, is hydrogenated to form the corresponding saturated compound in which the same two groups are alkyl or isoalkyl. It has been found that this synthesis route is preferred in cases where it is desired to obtain a compound of general formula (I) in which $R_1$ is propyl, butyl or isobutyl and $R_3$ is an alkyl group different from $R_1$, particularly because the alkylation step leading to the compound of general formula (III) gives better yields with an alkylating agent of the formula

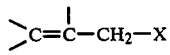

where X is as defined above.

The catalytic hydrogenation of the alkenyl or isoalkenyl group or of the two alkenyl or isoalkenyl groups is carried out in a good solvent for the xanthines, such as methanol, ethanol or ethyl acetate, in the presence of a hydrogenation catalyst, such as Raney nickel, palladium on active carbon (Pd/C) or platinum oxide. It is generally preferred to use ethanol and Pd/C. Although the reaction can be carried out under excess pressure and under heat, normal conditions, i.e. ambient temperature and atmospheric pressure, are preferred.

(c) A compound of formula

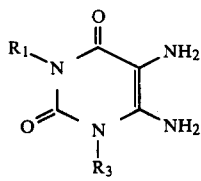

may be reacted with an acid of the formula $R_8$—COOH (where $R_1$, $R_3$ and $R_8$ are as defined above except that $R_1$ and $R_3$ are other than isopropyl) and the compound obtained cyclised. In this variant, which is preferably used for preparing compounds of general formula (I) in which $R_1$ and $R_3$ are identical, but other than isopropyl, a urea identically substituted in the one-position and three-position is used as the starting material and is treated with cyanoacetic acid in the presence of acetic anhydride and then with sodium hydroxide in accordance with Traube's classical synthesis to form a 1,3-dialkyl-6-aminouracil which is then converted into the compounds of general formula (III) in accordance with the following reaction scheme which enables the alkylation step to be avoided:

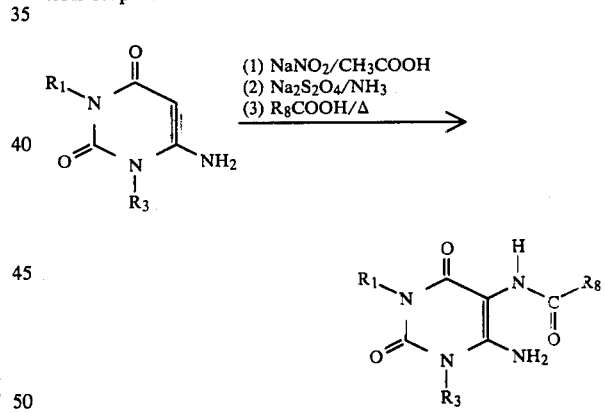

The compound of general formula (III) thus obtained is then cyclised as indicated above in reference to process a to form the corresponding compound of general formula (I).

(d) A final process comprising reacting a compound corresponding to the formula

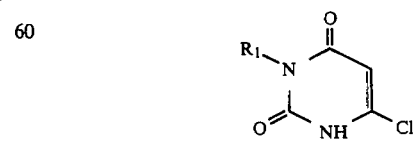

with an alkylating agent of the formula $R_3$—X, treating the compound obtained with an amine of the formula $R_8$—$CH_2$—$NH_2$ where $R_1$, $R_3$, X and $R_8$ are as defined above, to form a compound corresponding to the following formula

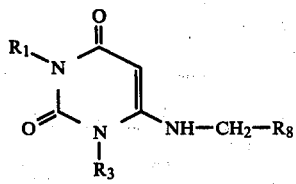

which is converted into a 5-nitroso derivative corresponding to the formula

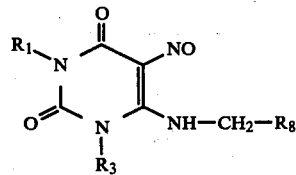

which cyclises spontaneously or which is cyclised by heating.

This final process is particularly applicable to compounds of general formula (I) in which at least one of the groups $R_1$ and $R_3$ is isopropyl. The process is similar to the process described by Goldner, Dietz and Carstens, for example in Justus Liebigs Ann. Chem. 691, 142, 1966.

A monosubstituted urea corresponding to the formula

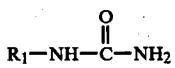

is used as the starting material and is reacted with diethyl malonate in ethanol in the presence of sodium ethylate to form a 1-substituted barbituric acid which is then reacted with a chlorinating agent, for example phosphorus oxychloride, to form a 6-chlorouracil, the substituent $R_1$ then being situated in the three-position. The 6-chlorouracil is then treated with an alkylating agent $R_3$—X to form a 1-$R_3$, 3-$R_1$-dialkyl-substituted uracil. In the presence of an amine of the formula $R_8$—$CH_2$—$NH_2$, this uracil gives the 6-amino derivative into which the nitroso group is introduced, for example using isopentyl nitrite in the 5-position, to form the uracil corresponding to general formula (IV) below. This uracil (IV) cyclises either spontaneously or by heating to form a xanthine corresponding to general formula (I), as shown in the following reaction scheme:

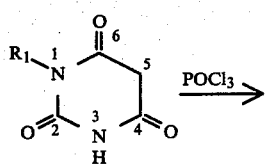

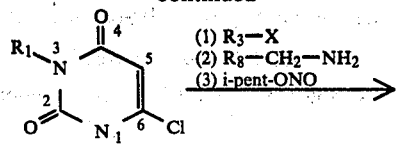

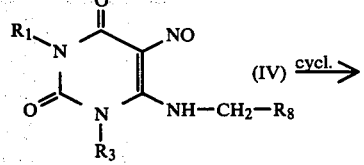

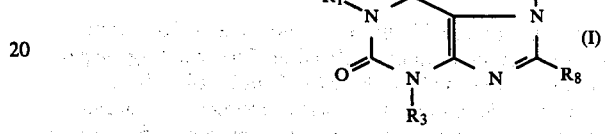

The present invention also relates to a pharmaceutical composition containing a compound of general formula (I) in an active quantity for the neuroleptic effect in combination with an inert pharmaceutically acceptable support.

The medicament according to the invention may be made up in various pharmaceutical forms containing the usual exipients or vehicles, such as tablets, capsules, suppositories, solutions, suspensions, and may be administered orally, sublingually, rectally, subcutaneously, intramuscularly, intravenously or by inhalation in doses of from 0.0004 to 0.04 g per day.

The invention is illustrated by the following Examples in which the quantities quoted represent quantities by weight unless otherwise indicated:

EXAMPLE 1

Synthesis of 1-allyl-3-butyl-8-methyl xanthine (1) 1-butyl-6-aminouracil 115 g (1 mole) of butyl urea and 94 g (1.1 mole) of cyanoacetic acid are heated for 2 hours at 75° to 80° C. in 200 ml of acetic anhydride. The mixture is cooled and 500 ml of ether are added. The precipitate is collected, washed with ether and dried.

The product thus obtained is suspended in a mixture of 300 ml of water and 150 ml of ethanol. After the resulting suspension has been heated to 85° C., 75 ml of a 10% aqueous NaOH solution are slowly added. The solid solubilises and shortly afterwards the uracil begins to precipitate. On completion of the addition, the mixture is left to react for another 30 minutes. The reaction product is acidified to pH 5 with HCl, left to cool and the precipitate is filtered. After washing with ice water, 100 g of colourless powder-form crystals are obtained.

(2) 1-butyl-5-nitroso-6-aminouracil 91.5 g (0.5 mole) of 1-butyl-6-aminouracil are suspended in 1 liter of water in a reactor equipped with a magnetic stirrer. A solution of 38 g of sodium nitrite in 250 ml of water is added to the suspension. 65 ml of acetic acid are then run in dropwise with stirring, after which the mixture is stirred for 18 hours at ambient temperature. After cooling in an ice bath, the precipitate is filtered, giving 90 g of violet-coloured crystals.

(3) 1-butyl-5,6-diaminouracil 84.8 g (0.4 mole) of 1-butyl-5-nitroso-6-aminouracil are suspended in 440 ml of a concentrated 50% aqueous solution of ammonium hydroxide. The resulting suspension is heated to 80° C. 88 g (0.48 mole) of sodium dithionite are added in portions with stirring over a period of 30 minutes. Stirring is then continued for 30 minutes at 80° C. and then overnight at room temperature. The product is cooled in ice, the precipitate is filtered and then washed with a little ice water, giving 62 g crystals in the form of a very fine powder.

(4) 1-butyl-5-acetylamino-6-aminouracil 59.4 g (0.3 mole) of 1-butyl-5,6-diaminouracil are refluxed for 2 hours with stirring in 240 ml of acetic acid in a reactor equipped with a condenser. The acetic acid is evaporated and the residue is taken up in a little ethanol which is then evaporated. This operation is repeated until a semi-crystalline residue is obtained. The semi-crystalline residue thus obtained is then triturated until solidification is complete. The solid is filtered and washed with ether, giving 72 g of fine, faintly yellow crystals.

(5) 1-allyl-3-butyl-8-methyl xanthine 13.2 g (0.055 mole) of 1-butyl-5-amino-6-acetylamino uracil are dissolved in 110 ml of dimethyl formamide. 2.4 g (0.06 mole) of NaOH and 7.3 g (0.06 mole) of allyl bromide are added to the resulting solution with stirring. The reaction takes place at ambient temperature over a period of from 30 to 60 minutes.

After the reaction mixture has been neutralised to pH 5 with a concentrated solution of HCl, the dimethyl formamide is evaporated. The oily residue is dissolved in 40 ml of a 10% NaOH solution and the resulting solution is refluxed for 2 hours. The product is then cooled to ambient temperature, washed with dichloromethane (2×10 ml) and adjusted to pH 5 with a concentrated HCl solution. The precipitate is extracted with dichloromethane (3×20 ml), after which the solution is dried and evaporated, giving 6.5 g of coloured crystals.

The crystals are decoloured by treatment with active carbon for 1 hour in boiling ethanol. Recrystallisation from a 1:1 mixture of ethanol and water gives colourless woolly crystals. Melting point (Mp): 170°–171° C. Nuclear magnetic resonance spectrum of the carbon (C-NMR): see Table 2 below.

EXAMPLES 2 TO 10

Following the procedure described in Example 1, the compounds are prepared using the appropriate reactants containing the groups $R_1$, $R_3$ and $R_8$, i.e. respectively: the monosubstituted urea in step 1, the carboxylic acid in step 4 and the alkylating agent in step 5, as shown in Table 1 below. Table 2 below shows the recrystallisation solvent, the melting points and the NMR values of the carbon.

TABLE 1

| Example No. | Compound | Urea (step 1) | Acid (step 4) | Alkylating agent (step 5) |
|---|---|---|---|---|
| 2 | 1-allyl-3-butyl xanthine | butyl urea | formic | allyl bromide |
| 3 | 1-allyl-3-isobutyl xanthine | isobutyl urea | formic | allyl bromide |
| 4 | 1-allyl-3-isobutyl-8-methyl xanthine | isobutyl urea | acetic | allyl bromide |
| 5 | 1-allyl-3-butyl-8-ethyl xanthine | butyl urea | propionic | allyl bromide |
| 6 | 1-allyl-3-propyl-8-methyl xanthine | propyl urea | acetic | allyl bromide |
| 7 | 1-allyl-3-isopentyl-8-methyl xanthine | isopentyl urea | acetic | allyl bromide |
| 8 | 1-ethyl-3-butyl-8-methyl xanthine | butyl urea | acetic | diethyl sulphate |
| 9 | 1,8-diethyl-3-butyl xanthine | butyl urea | propionic | diethyl sulphate |
| 10 | 1-butyl-3-allyl-8-methyl xanthine | allyl urea | acetic | butyl p-toluene sulphonate |

EXAMPLE 11

Synthesis of 1-propyl-3-butyl-8-methyl xanthine 5 g of 1-allyl-3-butyl-8-methyl xanthine (Example 1) are dissolved in 100 ml of ethanol in a hydrogenation apparatus, followed by the addition of 500 mg of Pd (10%)/C. Hydrogenation is carried out at ambient temperature until the consumption of hydrogen is over (approximately 1 hour). The mixture is filtered under heat, the precipitate is washed with ethanol and the solvent is evaporated from the filtrate, leaving 5 g of colourless crystals which are recrystallised from methanol. Mp: 174°–175° C. C-NMR (Table 2).

EXAMPLES 12 AND 13

Following the procedure described in Example 11, 1-propyl-3-isobutyl-8-methyl xanthine is prepared from 1-allyl-3-isobutyl-8-methyl xanthine (Example 4) and 1-butyl-3-propyl-8-methyl xanthine is prepared from 1-butyl-3-allyl-8-methyl xanthine (Example 10).

The melting point, the recrystallisation solvent and the NMR values of the carbon of these compounds are shown in Table 2 below.

EXAMPLE 14

Preparation of 1,3-dipropyl-8-methyl xanthine

(1) 1,3-dipropyl-6-aminouracil 37.5 g (0.26 mole) of 1,3-dipropyl urea and 22.5 g (0.26 mole) of cyano acetic acid are heated for 2 hours to 70° C. in 125 ml of acetic anhydride. The acetic anhydride is then evaporated, leaving approximately 90 g of an oily residue.

290 ml of a 10% aqueous NaOH solution are slowly added with stirring to this residue. The mixture undergoes a spontaneous increase in temperature and the oil dissolves. Soon afterwards, a precipitate is formed. It is left to cool to ambient temperature, precipitated, washed with water and dried, giving 55 g of a faintly yellow crystalline powder.

(2) 1,3-dipropyl-5-nitroso-6-aminouracil

This compound is prepared in the same way as in Example 1, step 2.

(3) 1,3-dipropyl-5,6-diaminouracil

This compound is prepared in the same way as in Example 1.3.

(4) 1,3-dipropyl-5-acetylamino-6-aminouracil

This compound is prepared in the same way as in Example 1.4.

(5) 1,3-dipropyl-8-methyl xanthine 15 g of 1,3-dipropyl-5-acetylamino-6-aminouracil (4) are refluxed for 1 hour in 150 ml of a 10% aqueous NaOH solution. The solution is cooled and acidified to pH 2 with concentrated HCl. The precipitate formed is filtered, washed with water and dried, leaving 13 g of colourless crystals.

The crystals thus obtained are decoloured by treatment with active carbon for 1 hour in a 1:1 mixture of ethanol and water. Recrystallisation from a mixture of the same composition gives colourless woolly crystals melting at 202° to 203° C. C-NMR (Table 2)

EXAMPLE 15

1,3-diisobutyl-8-methyl xanthine is prepared from 1,3-diisobutyl urea by the process described in Example 14. The Mp, recrystallisation solvent and C-NMR values are shown in Table 2 below.

EXAMPLE 16

Preparation of 1-isopropyl-3-butyl-8-methyl xanthine (1) 1-isopropyl barbituric acid 13.8 g (0.6 mole) of sodium are dissolved in 250 ml of anhydrous ethanol. 61.2 g (0.46 mole) of diethyl malonate and 47.3 g of isopropyl urea (0.46 mole) are added to the resulting solution. The mixture thus formed is heated for 7.5 hours to 120° C. (temperature of the bath). After cooling, a solution of concentrated HCl and water (1:4) is slowly added until the precipitate formed during the reaction has dissolved. The resulting solution is evaporated until a precipitate appears and is then left standing at 0° C. The precipitate is then filtered, washed with cold water and dried, giving 75 g of colourless crystals.

(2) 3-isopropyl-6-chlorouracil 350 ml of phosphorus oxychloride containing 15 ml of water are slowly run into 75 g (0.44 mole) of 1-isopropyl barbituric acid. After the violent exothermic reaction has abated, the reaction mixture is refluxed for 1 hour. The excess $POCl_3$ is removed by evaporation in vacuo and the oily residue is poured onto ice, giving a precipitate which is filtered, washed with ice water and dried. 55 g of yellowish crystals are thus obtained.

(3) 1-butyl-3-isopropyl-6-chlorouracil 16.6 g (0.12 mole) of potassium carbonate and 24 g (0.105 mole) of butyl-p-toluene sulphonate are added to a solution of 19 g (0.10 mole) of 3-isopropyl-6-chlorouracil in 200 ml of dimethyl formamide. The mixture is heated for 1 hour to 80° C. After evaporation of the solvent, the residue is taken up in water, followed by extraction with $CH_2Cl_2$. The extract is dried over $Na_2SO_4$ and the solvent is evaporated, leaving 24 g of a pale yellow oily product.

(4) 1-butyl-3-isopropyl-6-ethylaminouracil 100 ml of ethanol and 100 ml of a 70% ethylamine solution in water are added to the above oil (0.1 mole). The whole is then refluxed for 2 hours and evaporated to dryness, giving 25 g of a yellow oily product which is further used without purification.

(5) 1-isopropyl-3-butyl-8-methyl xanthine

The above oil is dissolved in 100 ml of ethanol. 30 drops of an ethanolic HCl solution are then added, followed by the introduction with stirring of 25 ml of isopentyl nitrite (slow addition, 15 minutes). The mixture is then left reacting for another hour, the solution obtained being deep violet in colour. The solution is evaporated to dryness, the residue is dissolved in dilute NaOH and the resulting solution is acidified to pH 2 with concentrated HCl. After standing at 0° C., the precipitate formed is filtered, dissolved in chloroform and the resulting solution filtered through a column containing 50 g of silica gel (eluent: chloroform). 10 g of faintly coloured crystals are thus obtained. The product is recrystallised twice from a 1:1 mixture of ethanol and water, giving fine colourless crystals melting at 172° to 173° C. C-NMR (Table 2).

TABLE 2

| Example No. | M.p. (°C.) | Recrystallisation solvent | C-NMR-values (CDCl$_3$, δ ppm) Reference: TMS (tetramethyl silane) |
|---|---|---|---|
| 1 | 170–171 | EtOH/H$_2$O 1:1 | 13.8; 14.8; 20.0; 30.2; 43.8; 43.8; 106.7; 117.3; 132.4; 149.7; 150.7; 152.4; 155.6; |
| 2 | 149–150 | MeOH | 13.8; 20.0; 30.2; 43.7; 43.9; 107.0; 117.5; 132.2; 140.6; 149.0; 157.7; 155.9; |
| 3 | 194–195 | EtOH/H$_2$O 1:1 | 20.0; 20.0; 27.4; 43.8; 51.0; 106.9; 117.5; 132.2; 140.5; 149.4; 151.0; 156.1; |
| 4 | 226–227 | EtOH/H$_2$O 1:1 | 14.8; 19.9; 19.9; 27.2; 43.7; 50.8; 106.5; 117.2; 132.4; 150.1; 151.0; 152.3; 155.6; |
| 5 | 153–154 | EtOH/H$_2$O 1:1 | 12.6; 13.8; 20.0; 22.7; 30.2; 43.7; 43.3; 106.7; 117.2; 132.5; 149.6; 150.8; 155.5; 157.4; |
| 6 | 186–187 | MeOH | 11.1; 14.8; 21.4; 43.7; 45.4; 106.6; 117.3; 132.4; 149.7; 150.7; 152.3; 155.6; |
| 7 | 171–172 | MeOH | 14.8; 22.5; 22.5; 26.1; 36.8; 42.6; 43.7; 106.7; 117.3; 132.4; 149.7; 150.6; 152.4; 165.6; |
| 8 | 214–215 | EtOH/H$_2$O 1:1 | 13.3; 13.8; 14.7; 20.0; 30.2; 36.9; 43.7; 106.8; 149.5; 150.7; 152.1; 155.7; |
| 9 | 153–154 | EtOH/H$_2$O 1:1 | 12.5; 13.3; 13.8; 20.0; 22.7; 30.3; 36.9; 43.7; 106.9; 149.4; 150.9; 155.7; 157.1; |
| 10 | 196–197 | MeOH | 13.8; 14.7; 20.3; 30.2; 41.7; 45.7; 106.8; 117.8; 131.6; 149.2; 150.7; 152.2; 155.8; |
| 11 | 174–175 | MeOH | 11.4; 13.8; 14.7; 20.0; 21.5; 30.2; 43.3; 43.8; 106.8; 149.5; 151.0; 152.1; 155.9; |
| 12 | 230–231 | MeOH | 11.4; 14.7; 19.9; 19.9; 21.4; 27.3; 43.3; 50.8; 106.7; 149.9; 151.2; 152.0; 155.9; |
| 13 | 189–190 | EtOH/H$_2$) 1:1 | 11.1; 13.8; 14.7; 20.3; 21.4; 30.2; 41.6; 45.4; 106.8; 149.6; 150.9; 152.1; 155.9; |
| 14 | 202–203 | EtOH/H$_2$O 1:1 | 11.1; 11.5; 14.7; 21.4; 21.4; 43.3; 45.4; 106.8; 149.5; 151.0; 152.1; 155.8; |
| 15 | 241–242 | EtOH/H$_2$O 1:1 | 14.7; 19.9; 19.9; 20.3; 20.3; 27.2; 27.4; 48.6; 50.8; 106.7; 149.9; 151.5; 152.0; 156.1; |

TABLE 2-continued

| Example No. | M.p. (°C.) | Recrystal- lisation solvent | C-NMR-values (CDCl$_3$, δ ppm) Reference: TMS (tetramethyl silane) |
|---|---|---|---|
| 16 | 172–173 | EtOH/H$_2$O 1:1 | 13.8; 14.8; 19.7; 19.7; 20.1; 30.2; 43.7; 46.4; 107.1; 149.4; 150.9; 152.0; 156.5; |

EXAMPLE 17

The xanthines obtained in accordance with the preceding Examples were the subject of a behavioural study in rats as a function of the anxiety induced by a new environment. In rats, anxiety is manifested by rearing the animal on its two hind paws, whilst locomotive activity is expressed by their movements.

Method

A state of anxiety is induced by confronting "naive" male Sprague-Dawley (Iffa-Credo, France) rats weighing from 260 to 300 g with a new environment in the form of cages of Macrolon (30×25 cm) which are situated in a sound-proofed air-conditioned room (22° C./50% relative humidity).

The number of rearings and movements is automatically determined by means of infrared photoelectric cells which only emit electrical pulses for the active movements of the animal and not for its static movements, such as those of its head and tail, for reasons of reproducibility. These photoelectric cells scan the cages at two different levels so as to distinguish the standing-up movements from the other movements. The number of rearings and movements is counted by the two rows of photoelectric cells, memorised and read out using a printer in accordance with a pre-established program.

The tested compound in solution in the form of its sodium salt is orally administered by oesophagus probe (the reference administration being formed by 6 ml/kg of distilled water) 30 minutes before the animals are placed in the cages. The number of rearings and movements is determined during the 15 minutes after they have been put into the cages in relation to the effect generated by the reference administration.

Evaluation of the Results

The ED 50 dose (expressed in mg/kg), i.e. the quantity of substance required to bring about a 50% variation in the motive activity in relation to the reference administration, is determined from the development of the effects of the tested substances on the number of movements and rearings as a function of the progressive doses administered expressed as a percentage of the movements and rearings counted for the reference administration.

The regression curves for the displacements and rearings are established from the preceding data by the method described by Saubrie, P. J. Pharmacol, (Paris) 2 (1971) 457–472, the equation of these regression curves corresponding to the mean expressed in percent of the performances of the references as a function of the product by 10 of the logarithm of the doses (only the doses which do not reduce the motive activity by more than 75% are considered).

The gradients of the regression curves corresponding to the movements and to the rearings are compared by recording the value of the gradient of the movement curve on the abscissa (d) and the value of the gradient of the rearing curve on the ordinant (r) of a system of rectungular axes. These values demonstrate the effect-dose relation for a given substance.

The ratio of the gradient of the movements to that of the rearings is also determined, enabling the specificity of effect of a given substance on the anxiety state to be assessed.

The results obtained are shown in Table 3 below:

TABLE 3

| Compound of Ex. No. | ED 50 (mg/kg) | Gradient of the move- ments ≠ 0 (d) | Gradient of the rearings ≠ 0 (r) | Ratio of the grad- ients d/r | Effect |
|---|---|---|---|---|---|
| 1 | 0.14 | p<0.001 | p<0.01 | n.s. | S.N. |
| 2 | 1.60 | p<0.001 | p<0.001 | <1; p<0.001 | S.A. |
| 3 | 0.98 | p<0.001 | p<0.001 | <1; p<0.001 | S.A. |
| 4 | 0.25 | p<0.001 | p<0.01 | n.s. | S.N. |
| 5 | 6.24 | p<0.01 | p<0.001 | <1; p<0.001 | S.A. |
| 6 | 0.27 | p<0.001 | p<0.001 | <1; p<0.01 | S.A. |
| 7 | 1.03 | p<0.001 | p<0.01 | <1; p<0.01 | S.A. |
| 8 | 1.02 | p<0.05 | p<0.01 | <1; p<0.05 | S.A. |
| 9 | 2.38 | p<0.001 | p<0.001 | <1; p<0.001 | S.A. |
| 10 | 3.95 | p<0.01 | p<0.01 | n.s. | S.N. |
| 11 | 0.35 | p<0.001 | p<0.001 | <1; p<0.001 | S.A. |
| 12 | 0.25 | p<0.01 | p<0.01 | <1; p<0.001 | S.A. |
| 13 | 1.05 | p<0.01 | p<0.01 | <1; p<0.05 | S.A. |
| 14 | 0.37 | p<0.01 | p<0.001 | <1; p<0.01 | S.A. |
| 15 | 0.42 | p<0.01 | p<0.01 | n.s. | S.N. |
| 16 | 1.76 | p<0.05 | p<0.01 | n.s. | S.N. |
| chlorproma- zine | 21 | p<0.05 | p<0.05 | n.s. | S.N. |
| haloperidol | 1 | p<0.01 | p<0.01 | n.s. | S.N. |
| chlordiaze- poxide | 12 | p<0.01 | p<0.01 | <1; p<0.01 | S.A. |
| theophyl- | — | p<0.001 | n.s. | >1; p<0.001 | ? |

TABLE 3-continued

| Compound of Ex. No. | ED 50 (mg/kg) | Gradient of the movements ≠ 0 (d) | Gradient of the rearings ≠ 0 (r) | Ratio of the gradients d/r | Effect |
|---|---|---|---|---|---|
| line | | | | | |

Legend:
The gradients are compared by the "t" test at the probabilities p<0.05, p<0.01 and p<0.001
n.s. means that the gradient is not significantly different from 0 or that the ratio between the gradients of the movements and the rearings is not significantly different from 1.
S.N. means that the compound has a non-specific sedative effect.
S.A. indicates a sedative effect of anxiolytic character
P means psychostimulating

Conclusions

The effect of a substance is determined by its position relative to the curve d=r of gradient=1. The substances situated on this curve have a similar effect on the rearings and movements, being sedatives with a non-specific effect (S.N.). For these compounds, the ED 50 value quoted corresponds to the mean taken from the two regression curves.

The substances for which the absolute value of the gradient of the rearings is significantly greater than that of the gradient of the movements have a specific effect on the anxiety state. These compounds are sedatives of anxiolytic character (S.A.). In this case, the ED 50 value is calculated from the regression curve of the reaction.

Table 3 above shows that the compounds of Examples 1, 4, 10, 15 and 16 have a similar action profile to the neuroleptics chlorpromazine and haloperidol,
that the compounds of Examples 2, 3, 5 to 9 and 11 to 14 have a similar action profile to chlordiazepoxide,
that theophylline is psychostimulating and does not have any effect on the anxiety state.

EXAMPLE 18

The compounds of Examples 1, 2, 4, 11 and 12 were subjected to toxicological tests:
(a) Determination of the acute toxicity LD 50 in male and female mice in solution in DMSO, the reference being DMSO alone, in accordance with J. T. Litchfield and F. Wilcoxon "Simplified method of evaluating dose-effect experiments", Journal of pharmacology and experimental therapy, Vol. 96, pages 99 to 113, 1949.
(b) Determination of the acute toxicity LD 50 in male and female rats in solution in DMSO (reference DMSO alone) in accordance with C. S. Veil and G. J. Wright "Intra- and inter laboratory comparative evaluation of single oral test", Toxicology and applied pharmacology, Vol. 11, pages 378–388, 1967.

The compounds of Examples 1, 2, 3, 4, 5, 9 and 11 showed the following activities in a base screening:
(c) diuretic in male rats, as determined in accordance with W. L. Lipschitz, Z Hadidian and A. Kerpcsar, JPET, Vol. 79, pages 97–110, 1943.
(d) anti-allergic in male and female rats, as determined in accordance with J. Goose and A. M. J. N. Blair, Immunol., Vol. 16, pages 749–760, 1969
(e) bronchodilatory in vitro as determined in accordance with F. P. Luduena et al., Arch. int. Pharmacodyn. Vol. 111, pages 392–400, 1957
(f) anti-histamine in vitro as determined in accordance with R. Magnus, Arch f.d., ges. physiol., Vol. 102, pages 123–151, 1904.

The results of these tests are set out in Table 4 below:

TABLE 4

| Compound of Example No. | a LD 50 in mg/kg p.o., mice | | b LD 50 in mg/kg p.o., rats | | c minimal effective dose in mg/kg producing a significant response | d | e minimal effective concentration in μg/ml producing a significant response | f |
|---|---|---|---|---|---|---|---|---|
| | male | female | male | female | | | | |
| 1 | 72 | 62 | 35 | 24 | 5 | 2.5 | 100 | 100 |
| 2 | — | — | >200 | >200 | 10 | 10 | 25 | 100 |
| 3 | — | — | — | — | 5 | no effect | no effect | 200 |
| 4 | 79 | 49 | 23 | 17 | 20 | 50 | no effect | no effect |
| 5 | — | — | — | — | 2.5 | no effect | 5 | 100 |
| 9 | — | — | — | — | 5 | no effect | 25 | 50 |
| 11 | 91 | 151 | 25 | 15 | 0.25 | no effect | 10 | 50 |
| 12 | — | — | 28 | 19 | — | — | — | — |

Legend: — means not tested

The compounds of Examples 1, 4, 11 and 12 were subjected to behavioural tests in accordance with "predictability and specificity of behaviour screening tests for neuroleptics", P. Worms and K. G. Lloyd, Pharmacology, Teratology, Vol. 5, pages 445–450, 1979, comprising:
catalepsy induced by haloperiodol in rats: potentialisation at 1 mg/kg p.o.
analgesia induced by pentobarbital in mice: potentialisation at 0.5 mg/kg p.o.
climbing behaviour induced by apomorphine in mice: inhibition at 1 mg/kg p.o.
stereotype behaviour induced by apomorphine in rats: no antagonism up to 8 mg/kg p.o.
rectal temperature in mice: hypothermal effect at 2 mg/kg p.o.
hypomotility induced by amphetamine in rats: antagonism at 0.5 mg/kg p.o.

These effects are typical of neuroleptics except that, unlike such neuroleptics as haloperidol or chlorpromazine, the above compounds have no effect upon stereotype behaviour in rats as induced by apomorphine.

We claim:
1. A compound corresponding to the formula

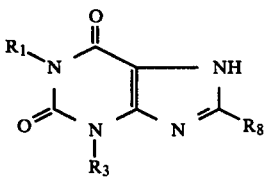 (I)

and physiologically acceptable salts thereof wherein:
$R_1$ is selected from the group consisting of $C_2$-$C_4$-alkyl, $C_3$-$C_4$-isoalkyl, $CH_2$-($C_2$-$C_3$-alkenyl), and $CH_2$-($C_3$-isoalkenyl);
$R_3$ is selected from the group consisting of $C_3$-$C_5$-alkyl, $C_3$-$C_5$-isoalkyl, $CH_2$-($C_2$-$C_4$-alkenyl), and $CH_2$-($C_3$-$C_4$-isoalkenyl); and
$R_8$ is selected from the group consisting of H, methyl and ethyl;
with the provisos that:
(1) when $R_8$ is H, $R_1$ is allyl;
(2) $R_1$ and $R_3$ cannot both represent butyl, isobutyl or allyl at the same time; and
(3) when $R_1$ is ethyl, $R_3$ is other than 2-methylbutyl; wherein the compound and its physiologically acceptable salts have neuroleptic activity.

2. A compound as claimed in claim 1, wherein $R_8$ is methyl and physiologically acceptable salts thereof, wherein the compound and its physiologically acceptable salts have neuroleptic activity.

3. A compound as claimed in claim 1, wherein $R_1$ is allyl, $R_3$ is butyl or isobutyl and $R_8$ is H and physiologically acceptable salts thereof, wherein the compound and its physiologically acceptable salts have neuroleptic activity.

4. A compound as claimed in claim 2, wherein $R_1$ is allyl, propyl or isobutyl and $R_3$ is propyl or butyl, and physiologically acceptable salts thereof, wherein the compound and its physiologically acceptable salts have neuroleptic activity.

5. 1-Allyl-3-butyl-8-methyl xanthine and physiologically acceptable salts thereof.

6. 1-Propyl-3-butyl-8-methyl xanthine and physiologically acceptable salts thereof.

7. 1-Allyl-3-isobutyl-8-methyl xanthine and physiologically acceptable salts thereof.

8. 1-Propyl-3-isobutyl-8-methyl xanthine and physiologically acceptable salts thereof.

9. 1,3-Dipropyl-8-methyl xanthine and physiologically acceptable salts thereof.

10. 1-Allyl-3-propyl-8-methyl xanthine and physiologically acceptable salts thereof.

11. A compound as claimed in claim 2, wherein $R_1$ is allyl or propyl and $R_3$ is propyl, butyl or isobutyl, and physiologically acceptable salts thereof, wherein the compound and its physiologically acceptable salts have neuroleptic activity.

12. A pharmaceutical composition comprising:
(a) an effective quantity of the compound claimed in any of claims 1-9, 10 or 11 or a physiologically acceptable salt thereof; and
(b) an inert carrier or diluent, to produce a neuroleptic effect.

13. A pharmaceutical composition comprising
(a) a compound corresponding to the formula

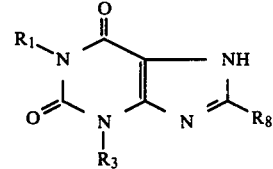 (I)

and physiologically acceptable salts thereof wherein:
$R_1$ is selected from the group consisting of $C_2$-$C_4$-alkyl, $C_3$-$C_4$-isoalkyl, $CH_2$-($C_2$-$C_3$-alkenyl), and $CH_2$-($C_3$-isoalkenyl);
$R_3$ is selected from the group consisting of $C_3$-$C_5$-alkyl, $C_3$-$C_5$-isoalkyl, $CH_2$-($C_2$-$C_4$-alkenyl), and $CH_2$-($C_3$-$C_4$-isoalkenyl); and
$R_8$ is selected from the group consisting of H, methyl and ethyl;
with the provisos that:
(1) when $R_8$ is H, $R_1$ is allyl; and
(2) $R_1$ and $R_3$ cannot both represent butyl, or allyl at the same time; and
(b) an inert carrier or diluent, to produce a neuroleptic effect.

14. 1-Allyl-3-butyl xanthine and physiologically acceptable salts thereof.

15. 1-Allyl-3-isobutyl xanthine and physiologically acceptable salts thereof.

16. 1-Allyl-3-butyl-8-ethyl xanthine and physiologically acceptable salts thereof.

17. 1-Allyl-3-isopentyl-8-methyl xanthine and physiologically acceptable salts thereof.

18. 1-Ethyl-3-butyl-8-methyl xanthine and physiologically acceptable salts thereof.

19. 1,8-Diethyl-3-butyl xanthine and physiologically acceptable salts thereof.

20. 1-Butyl-3-allyl-8-methyl xanthine and physiologically acceptable salts thereof.

21. 1-(Trans-2-butenyl)-3-propyl-8-methyl xanthine and physiologically acceptable salts thereof.

22. 1-Methallyl-3-propyl-8-methyl xanthine and physiologically acceptable salts thereof.

23. 1-Propyl-3-methallyl-8-methyl xanthine and physiologically acceptable salts thereof.

24. 1-Ethyl-3-pentyl-8-methyl xanthine and physiologically acceptable salts thereof.

25. 1-Ethyl-3-isopentyl-8-ethyl xanthine and physiologically acceptable salts thereof.

26. 1-Butyl-3-propyl-8-methyl xanthine and physiologically acceptable salts thereof.

27. 1-Isopropyl-3-butyl-8-methyl xanthine and physiologically acceptable salts thereof.

* * * * *

UNITED STATES PATENT AND TRADEMARK OFFICE
CERTIFICATE OF CORRECTION

PATENT NO. : 4,469,698
DATED : September 4, 1984
INVENTOR(S) : Georges Philippossian, et al.

It is certified that error appears in the above—identified patent and that said Letters Patent is hereby corrected as shown below:

Column 13, line 29, "reaction" should read --rearings--.

Signed and Sealed this

Twelfth Day of February 1985

[SEAL]

*Attest:*

DONALD J. QUIGG

*Attesting Officer*     *Acting Commissioner of Patents and Trademarks*